United States Patent [19]

Duffett et al.

[11] Plant 5,242

[45] Jun. 5, 1984

[54] CHRYSANTHEMUM PLANT NAMED FORTUNE

[75] Inventors: William E. Duffett, Salinas, Calif.; Grace H. Mack, New Canaan, Conn.

[73] Assignee: Yoder Brothers, Inc., Barberton, Ohio

[21] Appl. No.: 419,005

[22] Filed: Sep. 16, 1982

[51] Int. Cl.[3] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum cultivar named Fortune particularly characterized as to uniqueness by the combined characteristics of flat capitulum form, decorative capitulum type, light golden yellow ray floret color, diameter across face of capitulum up to 70 mm., short plant height, spreading branching pattern, average natural season flowering date of September 12, and average flowering response period of seven (7) weeks in photoperiodic controlled short day programs.

3 Drawing Figures

1

The present invention comprises a new and distinct cultivar of *Chrysanthemum morifolium,* Ramat., hereinafter referred to by the cultivar name Fortune.

Fortune is a product of a planned breeding program which had the objective of creating cultivars with decorative capitulum type, short plant height, spreading branching pattern, durable inflorescence, seven (7) week flowering response period, and yellow ray floret color under outdoor natural season conditions.

Fortune was originated from a cross made in a controlled breeding program planned and executed by Grace H. Mack in New Canaan, Conn. in the year 1975. The female parent was 959, a yellow decorative from a cross between M662×M617. The male parent was Patriot, a white decorative disclosed in U.S. Plant Pat. No. 3,897. Patriot was a cross between Snowbound×Pixie Cushion, disclosed in U.S. Plant Pat. No. 3,454.

Fortune was discovered and selected as a flowering plant within the progeny of the stated cross by Grace H. Mack in 1976 in an outdoor garden in New Canaan, Conn. The first act of asexual reproduction of Fortune was accomplished when vegetative cuttings were taken from the initial selection in 1977 in New Canaan, Conn. by Grace H. Mack. Subsequent asexual reproduction and horticultural examination in Salinas, Calif. by William E. Duffett of selected units initiated in 1979 has demonstrated that the combination of characteristics as herein disclosed for Fortune are firmly fixed and are retained through successive generations of asexual reproduction.

Fortune has not been observed under all possible environmental conditions. The phenotype may vary significantly with variation in environment such as temperature, light intensity, and day length. The following observations, measurements, and comparisons describe plants grown in a field in Salinas, Calif.

Rooted cuttings were established in soil in one gallon containers maintained outdoors under the natural temperature and day length prevailing during July through September. Single pinching was practiced with all branches and buds retained.

The following traits have been repeatedly observed and are determined to be basic characteristics of Fortune which in combination distinguish this chrysanthemum as a new and distinct cultivar:

2

(1) Flat capitulum form.
(2) Decorative capitulum type.
(3) Light golden yellow ray floret color.
(4) Diameter across face of capitulum up to 70 mm.
(5) Short plant height.
(6) Spreading branching pattern.
(7) Average natural season flowering date of September 12.
(8) Average flowering response period of seven (7) weeks in photoperiodic controlled flowering programs.

The accompanying photographic drawings show typical inflorescence and foliage characteristics of Fortune. Sheet 1 is a color photograph of Fortune. Sheet 2 is a black and white photograph showing three views of inflorescence of Fortune. Sheet 3 is a black and white photograph showing the leaves of Fortune at three stages of growth (mature, intermediate, immature).

Of the many commercially available cultivars known to the present inventors, the most similar existing cultivar in comparison to Fortune is the cultivar Jackpot (U.S. Plant Pat. No. 3,277).

Reference is made to the attached Chart A which compares certain characteristics of Fortune with the same characteristics of Jackpot. It will be noted that in comparison to Jackpot, Fortune has a darker ray floret color, earlier average natural flower date, and smaller diameter across face of capitulum. The capitulum form, capitulum type, plant height, branching pattern, and plant spread of Fortune are similar to those of Jackpot.

In the following description, color references are made to The Royal Horticultural Society Color Chart. The color values were determined between 1:30 and 2:00 PM on Sept. 12, 1981 under 150 foot-candle light intensity at Salinas, Calif.

Botanical classification: *Chrysanthemum morifolium,* Ramat., cv Fortune

INFLORESCENCE

A. Capitulum:
*form.*—Flat.
*Type.*—Decorative.
*Permanence.*—3 To 4 weeks.

*Diameter across face.*—55 To 70 mm.

B. Corolla of ray florets:

*Color (abaxial).*—15B oxidizing to 15D.

*Color (adaxial).*—14B oxidizing to 14D.

C. Reproductive organs:

*Androecium.*—Present disc florets.

*Gynoecium.*—Present both ray and disc florets.

D. Disc florets

*Color.*—Approximately 9A.

PLANT

A. General appearance: Spreading branching pattern; short height.

B. Foliage:

*Color (abaxial).*—Approximately 146A.

*Color (adaxial).*—Approximately 147B.

CHART A

COMPARISON OF FORTUNE AND JACKPOT

| CULTIVAR | RAY FLORET COLOR | CAPITULUM FORM AND TYPE | AVERAGE NATURAL SEASON FLOWER DATE |
|---|---|---|---|
| FORTUNE | LIGHT | FLAT | SEPTEMBER 12 |

CHART A-continued

COMPARISON OF FORTUNE AND JACKPOT

| | | | |
|---|---|---|---|
| JACKPOT | GOLDEN YELLOW YELLOW | DECORATIVE FLAT DECORATIVE | SEPTEMBER 20 |

| CULTIVAR | PLANT HEIGHT | BRANCHING PATTERN AND SPREAD | DIAMETER ACROSS FACE OF CAPITULUM |
|---|---|---|---|
| FORTUNE | SHORT | SPREADING | 55 to 70 mm. |
| JACKPOT | SHORT | SPREADING | 50 to 75 mm. |

COMPARISONS MADE OF PLANTS GROWN UNDER NATURAL SEASON OUTDOOR FIELD CONDITIONS IN SALINAS, CALIFORNIA

We claim:

1. A new and distinct cultivar of *Chrysanthemum morifolium,* Ramat., plant known by the name Fortune and particularly characterized as to uniqueness by the combined characteristics of flat capitulum form, decorative capitulum type, light golden yellow ray floret color, diameter across face of capitulum up to 70 mm., short plant height, spreading branching pattern, average natural season flowering date of September 12, and average flowering response period of seven (7) weeks in photoperiodic controlled short day programs.

* * * * *

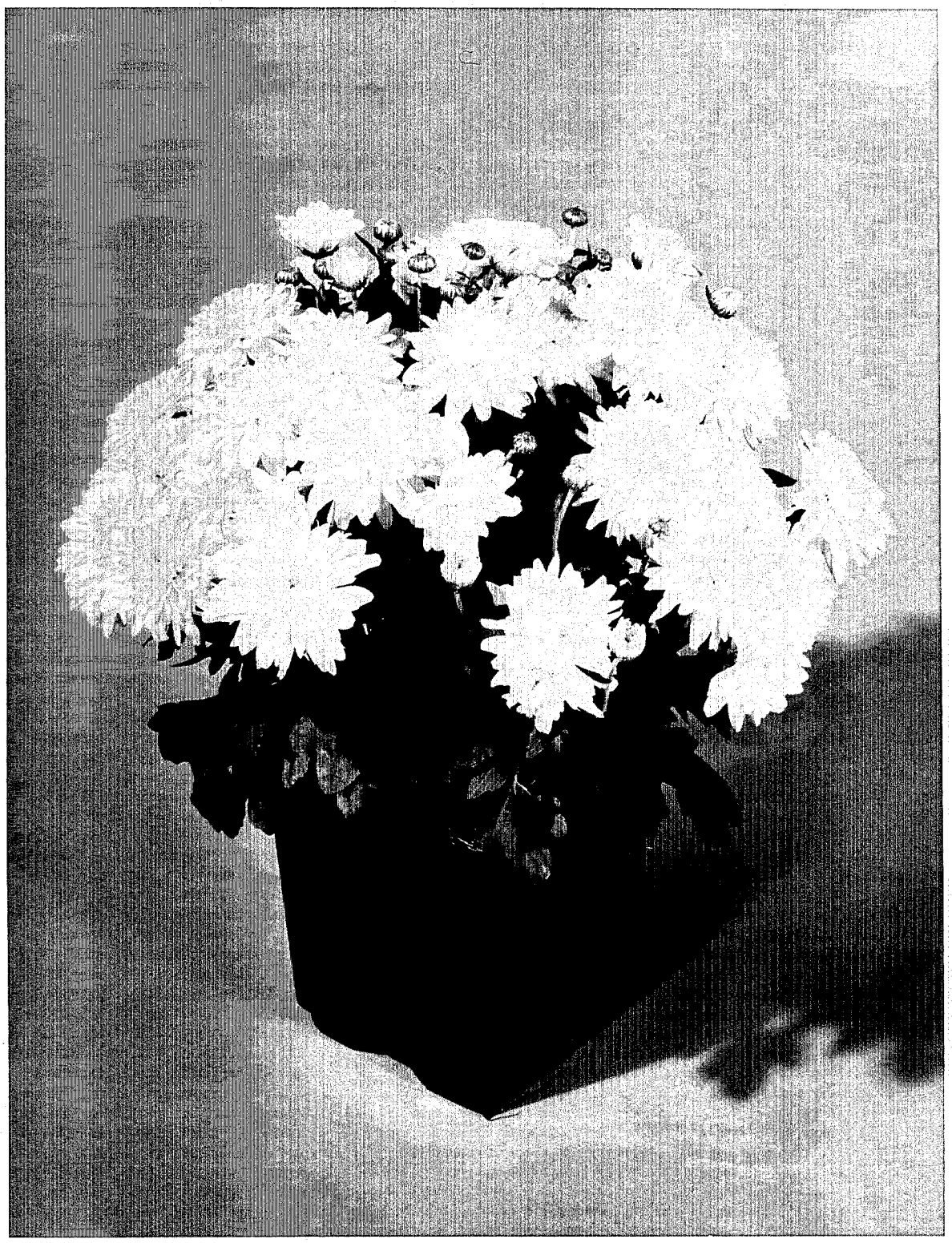

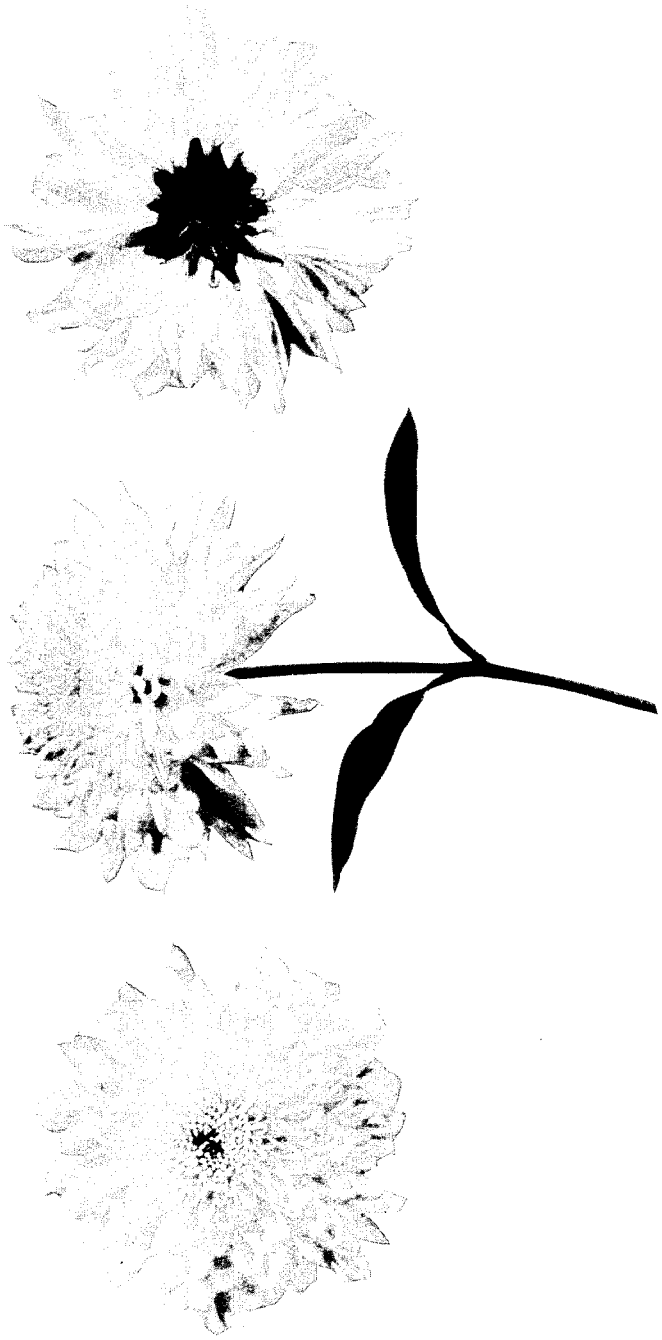

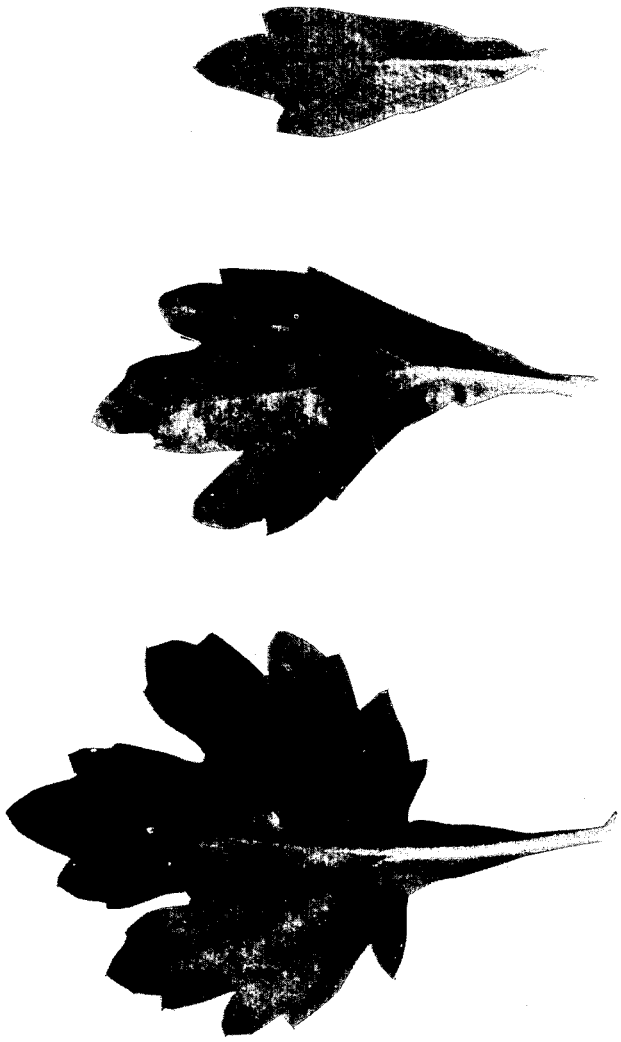

UNITED STATES PATENT AND TRADEMARK OFFICE

CERTIFICATE OF CORRECTION

PATENT NO. : PP 5242

DATED : June 5, 1984

INVENTOR(S) : Grace H. Mack et al

It is certified that error appears in the above-identified patent and that said Letters Patent is hereby corrected as shown below:

On the title page assignee should read:

--(73) Assignee: Grace H. Mack, New Canaan, Conn. --.

Signed and Sealed this

*Ninth* Day of *April 1985*

[SEAL]

*Attest:*

DONALD J. QUIGG

*Attesting Officer* *Acting Commissioner of Patents and Trademarks*